United States Patent [19]

Ruehle et al.

[11] Patent Number: 5,043,442

[45] Date of Patent: Aug. 27, 1991

[54] PROCESS OF PREPARING AN ISOTHIOCYANATE INTERMEDIATE USED IN THE PREPARATION OF XYLAZINE

[75] Inventors: Paul Ruehle, Gladstone, Mo.; Amy M. Bunker, Overland Park, Kans.

[73] Assignee: Chemsyn Science Laboratories, Lenexa, Kans.

[21] Appl. No.: 503,257

[22] Filed: Apr. 2, 1990

[51] Int. Cl.$^5$ .................. C07C 331/00; C07D 279/04
[52] U.S. Cl. ......................................... 544/53; 558/18
[58] Field of Search ............................. 558/18; 544/53

[56] References Cited

U.S. PATENT DOCUMENTS

| | | | |
|---|---|---|---|
| 2,595,723 | 5/1952 | Spiegelberg et al. | 558/18 |
| 3,235,550 | 2/1966 | Behner et al. | 544/53 |
| 3,341,564 | 9/1967 | Potts et al. | 544/53 |
| 4,614,798 | 9/1986 | Elliott et al. | 544/53 |

FOREIGN PATENT DOCUMENTS

| | | | |
|---|---|---|---|
| 700436 | 12/1940 | Fed. Rep. of Germany | 544/53 |
| 1009179 | 5/1957 | Fed. Rep. of Germany | 544/53 |
| 1935302 | 1/1971 | Fed. Rep. of Germany | 544/53 |
| 828991 | 6/1938 | France | 544/53 |
| 75-111027 | 2/1974 | Japan | 544/53 |
| 793802 | 4/1958 | United Kingdom | 544/53 |

OTHER PUBLICATIONS

Fujinami, et al., Decomposition of O-Ethyl N-Substituted Thiocarbamates and Carbamates with Butyl-Lithium and Carbon Disulfide or Sulfur Dioxide; Nippon Kagaku Kaishi 1978, (5), 773–4 (Japan).

Shahak, et al.; Conversion of Amides to Thiol Acids and Isothiocyanates. A Novel Method for Breaking of the Amide Bond; Journal of the American Chemical Society/ 95.10/May 16, 1973, pp. 3340–1 (U.S.).

*Primary Examiner*—Mary C. Lee
*Assistant Examiner*—Robert C. Whittenbaugh
*Attorney, Agent, or Firm*—Litman, McMahon & Brown

[57] ABSTRACT

A process for preparing 2,6-dimethylphenylisothiocyanate comprises the steps of dissolving 2,6-dimethylaniline in carbon disulfide and ammonium hydroxide to form a dithiocarbamate salt. The salt is reacted with ethyl chloroformate to form 2,6-dimethylphenylisothiocyanate, which may thereafter be reacted with 3-amino-1-propanol and subsequently cyclized, by treating with hydrochloric acid, to form xylazine.

11 Claims, No Drawings

PROCESS OF PREPARING AN ISOTHIOCYANATE INTERMEDIATE USED IN THE PREPARATION OF XYLAZINE

BACKGROUND OF THE INVENTION

This invention relates to an improved process for the preparation of xylazine. More particularly, the invention is directed to an improvement in the production of an isothiocyanate intermediate (2,6-dimethlyphenylisothiocyanate) used in the preparation of xylazine.

Xylazine is a well known sedative, analgesic, and muscle relaxant, and has been produced by various alternatives synthesis. One of the most common synthesis sequences is listed below:

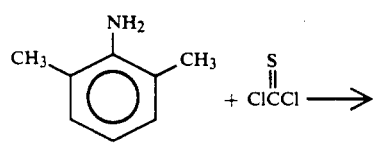

2,6-dimethylaniline     thiophosgene

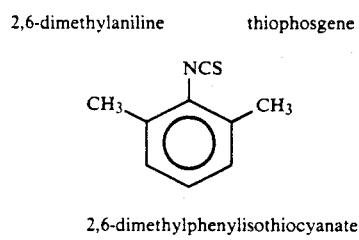

2,6-dimethylphenylisothiocyanate

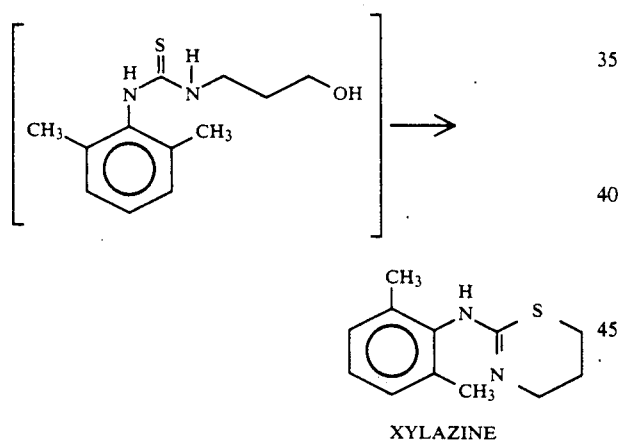

XYLAZINE

The reaction sequence shown involves the reagent thiophosgene which gives high yields of the intermediate 2,6-dimethylphenylisothiocyanate directly from 2,6-dimethylaniline. However, this synthesis is undesirable because of the toxicity of thiophosgene, and because thiophosgene has now become prohibitively expensive and nearly unavailable in bulk quantities.

A second reaction sequence is provided in the U.S. Pat. No. 4,614,798 to Elliott, et al., and is as follows:

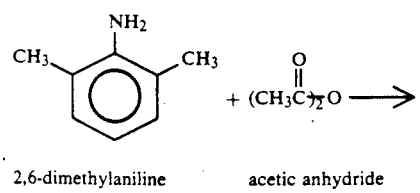

2,6-dimethylaniline     acetic anhydride

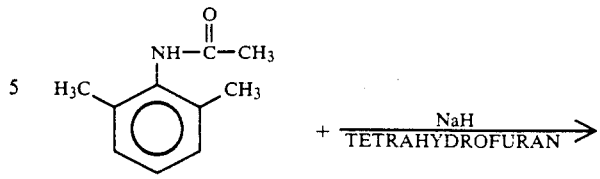

N-2,6 dimethylphenylacetamide

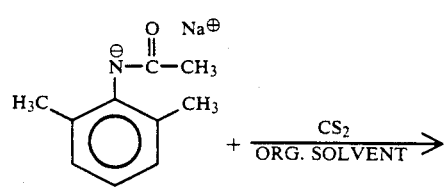

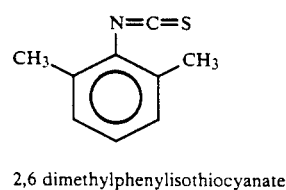

2,6 dimethylphenylisothiocyanate

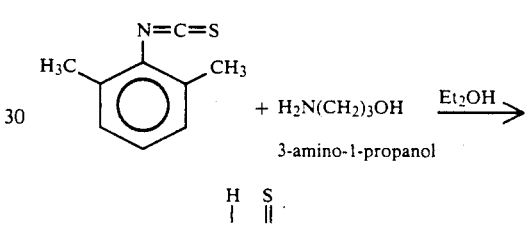

3-amino-1-propanol

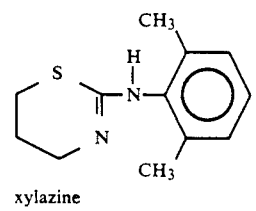

thiourea derivative xylazine

However, the reaction sequence shown is not desirable because of dangers associated with both handling large amounts of sodium hydride and the evolution of large volumes of hydrogen gas during the addition of the hydride to the solution containing 2,6-dimethylacetanilide. Another disadvantage arises because at the evolution of heat and vigorous foaming during the addition of sodium hydride, with the potential of a runaway reaction. Yet another disadvantage arises because the potential for an explosion exists during the quenching of the reaction mixture with water after the addition of carbon disulfide if residual sodium hydride is present.

A final disadvantage arises in the distillation of the isothiocyanate from this reaction sequence. Difficulty is often encountered during the distillation due to the presence of unconverted 2,6-dimethylacetanilide. The latter compound distills at a temperature similar to that temperature at which the isothiocyanate distills, and complicates the distillation due to solidification of 2,6-dimethylacetanilide in the distillation head.

Thus, because the synthesis of xylazine according to the present invention does not involve the addition of a moisture sensitive and potentially pyrophoric reagent such as sodium hydride to the reaction mixture with the dangers associated with the evolution of hydrogen and foaming, it is well suited for large scale production of xylazine. Furthermore, because of the nature of the isothiocyanate intermediate formed with the method of the present invention, the ease of purification of the associated intermediate by vacuum distillation is improved.

OBJECTS OF THE INVENTION

Accordingly, the principal objects of the present invention are: to provide an improved process for the preparation of xylazine; to provide such a process which minimizes the use of highly toxic or hazardous reagents; to provide such an improved process which uses readily available reagents; to provide such an improved process which uses commercially available reagents which are not prohibitively expensive; to provide such a process producing relatively high yields of xylazine; and to provide such an improved process which is particularly well adapted for the indicated usage thereof.

Other objects and advantages of this invention will become apparent from the following description wherein it is set forth by way of illustration and example, certain embodiments of the invention.

SUMMARY OF THE INVENTION

A process is provided for preparing 2,6-dimethylphenylisothiocyanate which is an intermediate in the preparation of xylazine, a compound which is used as a sedative, an analgesic and a muscle relaxant in warm blooded animals. According to the process of the present invention, 2,6-dimethylaniline is first dissolved in carbon disulfide and ammonium hydroxide to form a dithiocarbamate salt. The salt is reacted with ethyl chloroformate to form the intermediate 2,6-dimethylphenylisothiocyanate, which is thereafter reacted with 3-amino-1-propanol and subsequently cyclized, by treating with hydrochloric acid to form xylazine.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art variously employ in the present invention in virtually any appropriately detailed reaction sequence.

In general, the present invention is the process of producing xylazine using the steps of reacting carbon disulfide, ammonium hydroxide, and ethyl chloroformate to form the intermediate 2,6-dimethylphenylisothiocyanate from 2,6-dimethylaniline. Carbon disulfide, ammonium hydroxide and ethyl chloroformate are desirable since they are neither highly toxic or dangerous, nor are they prohibitively expensive.

Preparation of 2,6-dimethylphenylisothiocyanate

According to the present invention, the preparation involves first adding 2,6 dimethylaniline to a cold mixture of carbon disulfide and ammonium hydroxide which when stirred gives a crystalline ammonium dithiocarbamate salt. However, other weak bases, as well as strong bases, such as sodium hydroxide or potassium hydroxide, are seen to be acceptable substitutes for ammonium hydroxide. The salt is isolated by filtration and then decomposed to 2,6-dimethylphenylisothiocyanate upon treatment with ethyl chloroformate in water and 2-propanol (or other commercially available alcohols). It is foreseen that other haloformate esters (such as ethyl bromoformate and methyl chloroformate) would be acceptable substitutes for ethylchloroformate.

The reaction path for production of 2,6-dimethylphenylisothiocyanate is specified below:

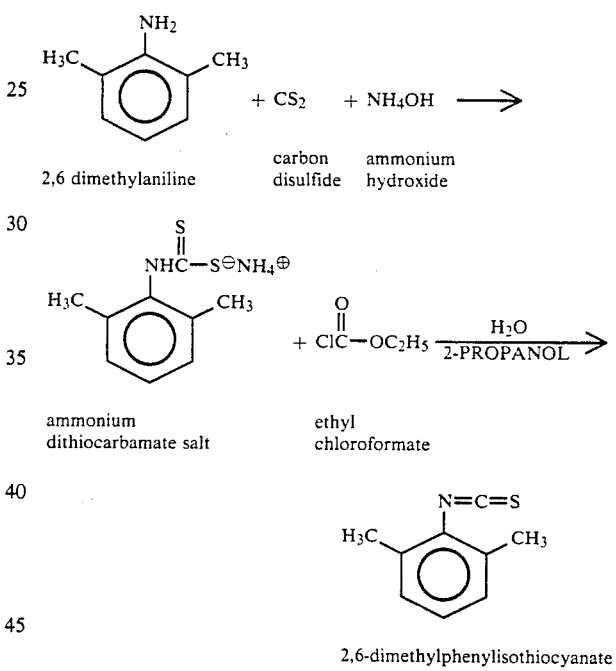

Preparation of Xylazine

The preparation of xylazine from 2,6-dimethylphenylisothiocyanate is well documented and is, for example, described in U.S. Pat. No. 3,235,550 to Behner, et al.; German Patent No. 1,173,475 (July 9, 1964); and Belgium Patent No. 634,552 (Jan. 6, 1964), all incorporated herein by reference. This synthesis comprises the reaction of 2,6-dimethylphenylisothiocyanate with 3-amino-1-propanol in polar solvent such as ether and thereafter refluxing the mixture for a period of time to form a thiourea derivative (or as used elsewhere herein, a thiourea).

The thiourea is then removed and concentrated hydrochloric acid is added to the thiourea with continued refluxing. The reaction mixture is cooled, treated with water, filtered and the filtrate made basic so as to form a precipitate which is recrystalized to produce xylazine according to the following process steps:

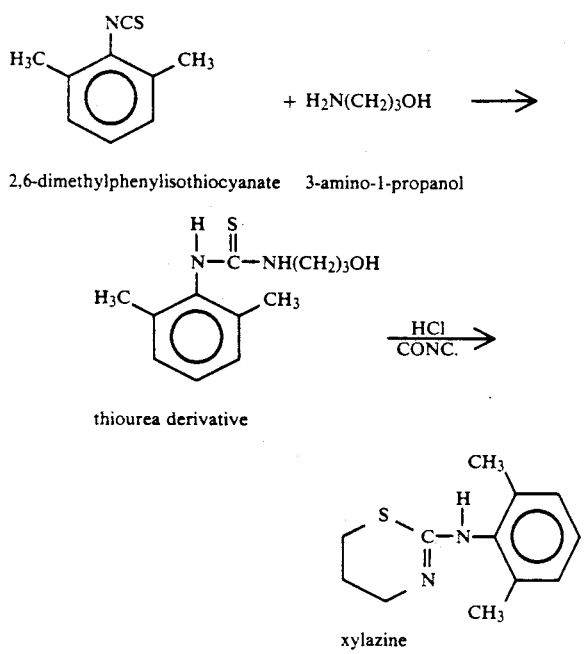

The following examples are included for the purpose of illustrating the invention and are not intended to limit the scope of the invention of the present application.

EXAMPLES

Xylazine was prepared according to the present invention by a synthesis that is discussed below.

745 grams (9.8 moles) of carbon disulfide and 1230 milliliters (ml) of concentrated ammonium hydroxide was added to a 5 liter, 3-neck flask fitted with a mechanical stirrer, teflon clad thermocouple, and an additional funnel. The contents of the flask were cooled to 0° C. by use of an ice bath. Then with rapid stirring, 1,008 grams of 2,6-dimethylaniline was added drop wise to the contents of the flask. The temperature was maintained below 10° C. by controlling the rate of addition. It is preferable to maintain the temperature in the range of about 10° C. to avoid a run away reaction (which run away begins to occur at a temperature of about 30° C. and is accompanied by a loss of ammonium ($NH_3$) and carbon disulfide ($CS_2$) gas). The addition took approximately 45 minutes. The reaction mixture (orange-red in color) was allowed to stir for an additional four hours, during which time a dithiocarbamate salt crystalized. The salt crystals were collected by suction filtration using a Buchner funnel, and were allowed to suck dry on the aspirator. The crystaline salt was placed in a 12-L flask fitted with a mechanical stir, thermo couple, and an addition funnel, and 5 liters of water with 2-propanol (water to propanol ratio of which ranged between 1:1 and 3:1 by volume, respectively) was added. Ethyl chloroformate (890.8 grams; 8.21 moles) was added dropwise to the stirred slurry at a rate such that the temperature did not rise above 40° C.; a cooling bath was used to help control the temperature. The addition funnel was replaced by a condenser, and the reaction mixture was heated to between 60° and 70° C. and maintained at this temperature for 1 hour. The reaction mixture was cooled to ambient temperature and then 1 liter of water was added. The layers were separated, and the bottom layer (2,6-dimethylphenylisothiocyanate) was washed with 200 ml of water and then dryed over anhydrous sodium sulfate. Distillation under vaccuum (125° Centigrade at about 3 torr.) gave 949 grams (55.2% yield on total theoretical basis by weight) of 2,6-dimethylphenylisothiocyanate. The intermediate product is filtered to remove any solid by-product prior to use in next step. The product was used directly in the next step of the synthesis.

The resulting 2,6-dimethylphenylisothiocyanate was shown to have a peak in the IR spectrum at 2150 $cm^{-1}$ (a characteristic peak for this product).

380 ml (373 grams, 4.97 moles) of 3-amino-1-propanol and 450 ml of tetrahydrofuran ("THF") were added to a 5-L flask fitted with a mechanical stirrer, teflon clad thermol-couple and an addition funnel. Then with rapid stirring, 749 grams (4.59 moles) of the 2,6-dimethylphenylisothiocyanate were added dropwise over a 2 hour period. The temperature was kept below 45° C. by controlling the rate of addition and by the use of a cooling bath. The cooling bath was removed, and replaced with a heating mantle. The temperature was raised to 50° C. followed by the addition of 435 ml. concentrated hydrochloric acid. The addition funnel was removed and a distillation head was placed on the flask. Heating was continued with the distillation of THF and water until the internal temperature had reached 95° C., which took about 2 hours. The reaction mixture was then diluted with 2 liters of water and the stirred solution was allowed to cool to room temperature. The aqueous solution was filtered through a 0.2 microfilter. The reaction mixture was made basic by the careful addition of 10% sodium hydroxide. The addition was continued until the pH of the solution was greater than or equal to 12. A solid was collected by filtration, washed with water and partially dryed in the funnel. The solid was then transferred into a flask fitted with a mechanical stirrer and 1 liter of acetone was added. The slurry was stirred for 1 hour using an ice bath to chill the mixture. The product was isolated by filtration, and air dryed to give 750 grams of crude xylazine. The product had a purity of 99% by GC analysis and gave a IR spectrum that was virtually identical to that of a standard sample of xylazine. The 80 MHz $1_H$ NMR spectrum ($CDCl_3$) produced the following results: delta 7.15 (bs, 3, ArH), 4.5 (t, 2, $CH_2$), 3.15 (t, 2, $CH_2$), 2.9–2.0 (m, 8, $CH_2$ and $CH_3$) was in complete agreement with a spectrum of a standard xylazine sample. Furthermore, the mixed melting point of the xylazine sample and a standard showed no depression.

The results of three pilot runs, generally according to the example reaction sequence specified above, are presented in Table 1 below (pilot test no. 2 was prepared exactly according to the example reaction sequence specified above).

TABLE 1

Percent Yield
(percent yield by weight of theoretical yield
for components used if complete conversion)

| Pilot Test No. | Percent Yield - 2,6-dimethylphenylisothiocyanate | Percent Yield Xylazine | Overall Yield (Percent) |
|---|---|---|---|
| 1 | 55.1% | 57.0% | 31.4% |
| 2 | 56.0% | 52.5% | 29.4% |
| 3 | 60.8% | 55.8% | 33.9% |

The results of the pilot tests demonstrate that carbon disulfide, ammonium hydroxide, and ethyl chloroformate can be used to economically and safely produce xylazine.

It is noted that any theories presented herein are for the purpose of attempting to understand the present invention and are not intended to be limiting upon the scope of the invention or the claims or binding as to the manner in which the processes of the invention function.

It is to be understood that while certain forms of the present invention have been illustrated and described herein, it is not to be limited to the specific processes or compositions described herein.

We claim:

1. A process for the preparation of xylazine; said process including the steps of:
   (a) adding 2,6-dimethylaniline to carbon disulfide and a base to produce a dithiocarbamate salt;
   (b) treating said salt with ethyl chloroformate to produce 2,6-dimethylphenylisothiocyanate;
   (c) reacting said 2,6-dimethylphenylisothiocyanate with 3-amino-1-propanol to produce a thiourea; and
   (d) reacting said thiourea with hydrochloric acid to produce xylazine.

2. The process according to claim 1 wherein:
   (a) said base is selected from the group consisting of weak bases.

3. The process according to claim 1 wherein:
   (a) said base is selected from the group consisting of strong bases.

4. The process according to claim 1 wherein:
   (a) said base is ammonium hydroxide.

5. The process according to claim 4 including the step of:
   (a) first cooling a mixture of the carbon disulfide and ammonium hydroxide to about 0° C. prior to adding the 2,6-dimethylaniline thereto.

6. The process according to claim 4 including the step of:
   (a) forming a mixture of carbon disulfide and ammonium hydroxide prior to addition of the 2,6-dimethylaniline; and
   (b) maintaining the temperature of said mixture below 10° Centigrade during the addition of the 2,6-dimethylaniline to said mixture.

7. The process according to claim 4 including the step of:
   (a) adding a mixture of water and 2-propanol in a ratio range of about 1:1–3:1 by volume to said ammonium dithiocarbamate salt prior to the addition of ethyl chloroformate thereto.

8. The process according to claim 4 including the step of:
   (a) maintaining the temperature of a mixture comprising said ammonium dithiocarbamate salt, the water and the 2-propanol below 40° C. during the addition of ethyl chloroformate thereto.

9. The process according to claim 4 including the step of:
   (a) heating a mixture comprising said ammonium dithiocarbamate salt, water, 2-propanol, and ethyl chloroformate with a range from about 60° to about 70° Centigrade and maintaining the mixture in said temperature range for about 1 hour after the addition of ethyl chloroformate to said mixture is complete.

10. The process according to claim 4 including the step of:
    (a) providing about 1.2 molar equivalents of carbon disulfide, from about 2.0 to 2.5 molar equivalents of ammounium hydroxide, and about 1.0 molar equivalents of ethyl chloroformate to each molar equivalent of dimethylaniline at the appropriate step of reaction.

11. The process according to claim 1 including the step of:
    (a) distilling the resultant mixture from step (b) of claim 1 under vaccuum of about 3 torr. and a temperature of about 125° Centigrade.

* * * * *